(12) United States Patent
Hofmann

(10) Patent No.: US 9,060,864 B1
(45) Date of Patent: Jun. 23, 2015

(54) JOINT PROSTHESIS

(71) Applicant: Aaron A. Hofmann, Las Vegas, NV (US)

(72) Inventor: Aaron A. Hofmann, Las Vegas, NV (US)

(73) Assignee: Hofmann Management Corporation, Salt Lake City, UT (US)

( * ) Notice: Subject to any disclaimer, the term of this patent is extended or adjusted under 35 U.S.C. 154(b) by 17 days.

(21) Appl. No.: 13/975,673

(22) Filed: Aug. 26, 2013

Related U.S. Application Data

(60) Provisional application No. 61/693,506, filed on Aug. 27, 2012.

(51) Int. Cl.
| | |
|---|---|
| *A61F 2/28* | (2006.01) |
| *A61F 2/30* | (2006.01) |
| *A61F 2/32* | (2006.01) |
| *A61F 2/38* | (2006.01) |
| *A61F 2/40* | (2006.01) |
| A61F 2/34 | (2006.01) |
| A61F 2/36 | (2006.01) |

(52) U.S. Cl.
CPC .............. *A61F 2/30767* (2013.01); *A61F 2/32* (2013.01); *A61F 2/38* (2013.01); *A61F 2/40* (2013.01); *A61F 2/30* (2013.01); *A61F 2/34* (2013.01); *A61F 2/36* (2013.01); *A61F 2310/00317* (2013.01); *A61F 2310/00874* (2013.01)

(58) Field of Classification Search
None
See application file for complete search history.

(56) References Cited

U.S. PATENT DOCUMENTS 8,357,205 B2   1/2013   Rahaman et al.

*Primary Examiner* — David H Willse
*Assistant Examiner* — Javier Blanco
(74) *Attorney, Agent, or Firm* — Lowry Blixseth LLP; Scott M. Lowry

(57) ABSTRACT

The improved joint prosthesis includes a metal-based substrate forming an articulatory surface for the joint prosthesis, wherein the metal-based substrate is coated with a ceramic or ceramic-based surface coating of a thin film doped silicon nitride ($Si_3N_4$) layer thereon, as disclosed in U.S. Pat. No. 6,881,229. The ceramic coating provides improvements in ultra-low wear over an extended service life, with dramatically reduced risk of brittle fracture when articulated or moved against articulation surfaces such as an acetabular cup in a hip prosthesis. In one preferred formation process, the ceramic coating is applied to the metal substrate by vapor deposition to mirror the surface finish of the substrate, and then polished to a smoother surface finish.

9 Claims, 4 Drawing Sheets

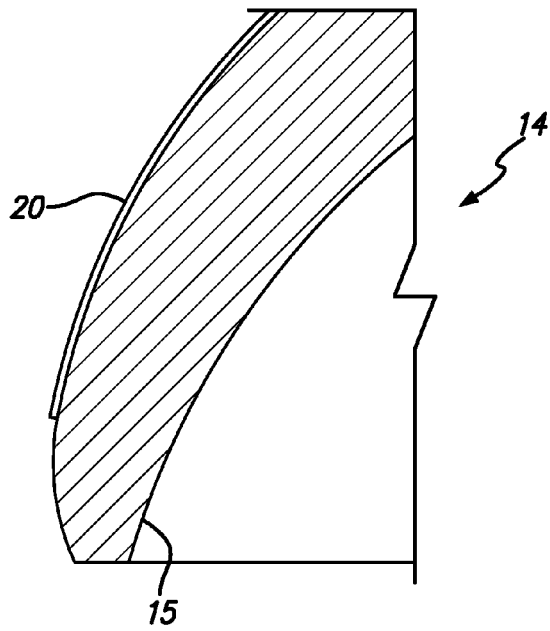
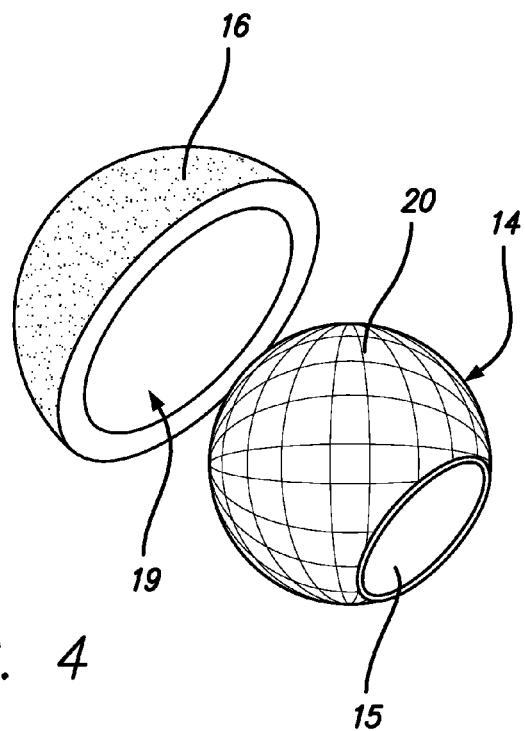

JOINT PROSTHESIS

BACKGROUND OF THE INVENTION

This invention relates generally to improvements in joint prostheses, particularly with respect to a ceramic-coated articulatory component such as a metal femoral ball in a hip prosthesis. The ceramic-coated articulatory component can be formed by vapor deposition of the like to have a relatively thin coating structure (about 5 microns) mirroring the surface finish or smoothness of the underlying metal substrate, and suitable for polishing to a smoother surface finish and a thinner coating structure (about 3-4 microns).

Joint prostheses such as hip prosthesis or knee prosthesis generally comprise a metal articulatory component fixed to patient bone and which moves against an associated bearing insert structure. In a typical hip or knee prosthesis, the articulatory component is formed from a biocompatible metal material such as cobalt chrome, titanium, or stainless steel to provide a strong and durable prosthetic base structure for engaging and moving against the associated bearing insert. In recent years, however, attempts have been made to construct the articulatory component from a ceramic or ceramic-based material to provide relatively smooth movement substantially in the absence of metal debris which can lead to prosthesis failure. One preferred ceramic-based material comprises silicon nitride, as disclosed in U.S. Pat. No. 6,881,229, which is incorporated by reference herein. Unfortunately, such ceramic materials have achieved relatively slow acceptance due to a fear of relatively low material toughness and associated fear of brittle fractures.

U.S. Pat. No. 6,881,229 discloses an improved ceramic material for use in joint prostheses, such as knee prostheses, wherein a ceramic-on-ceramic or a ceramic-on-metal articulatory interface is defined. The improved ceramic material comprises a doped silicon nitride ($Si_3N_4$) having relatively high hardness, tensile strength, elastic modulus, lubricity, and fracture toughness. Specifically, the improved doped silicon nitride ceramic has a flexural strength greater than about 700 Mega-Pascal (MPa) and a fracture toughness greater than about 7 Mega-Pascal root meter ($MPam^{0.5}$). This high strength and high toughness doped silicon nitride ceramic achieves ultra-low wear over an extended service life, with dramatically reduced risk of brittle fracture.

In addition, U.S. Pat. No. 6,846,327 discloses improved ceramic materials for bone graft applications, wherein the ceramic material is designed to mimic structural characteristics of natural patient bone by including first and second regions of comparatively lower and higher porosity to respectively mimic natural cortical and cancellous bone structures. The preferred ceramic materials disclosed exhibit a flexural strength greater than about 500 Mega-Pascal (MPa) and a fracture toughness greater than about 5 Mega-Pascal root meter ($MPam^{0.5}$). In use, the relatively low porosity region of the ceramic material provides high structural strength and integrity, whereas the higher porosity region is suitable for bone ingrowth to achieve secure and stable implant affixation.

The present invention comprises an improved joint prosthesis particularly wherein the articulatory component thereof is constructed from a metal substrate coated in the articulatory region with an improved high strength and high toughness ceramic material as disclosed, e.g., in U.S. Pat. No. 6,881,229 and/or U.S. Pat. No. 6,846,327, both references of which are incorporated by reference in their entireties.

SUMMARY OF THE INVENTION

The improved joint prosthesis disclosed herein includes an articulatory component constructed from a metal base material for relatively high strength, with an articulatory region having a relatively high strength and high toughness ceramic or ceramic-based coating defining at least one articulation surface for ultra-low wear articulation during joint movements. In a hip prosthesis, the articulatory component comprises a femoral component adapted for fixation to the upper end of the patient's femur, with a ball-shaped extension or head formed from the selected metal base material. At least a portion of the exterior or articulatory surface of this ball-shaped head is surface-coated with the ceramic or ceramic-based coating for articulation against and within the confines of an associated acetabular cup which may include a bearing component.

In the preferred form, the ceramic or ceramic-based coating comprises a doped silicon nitride ($Si_3N_4$) as disclosed in U.S. Pat. No. 6,881,229, which is incorporated by reference herein. This high strength and high toughness doped silicon nitride ceramic coating provides improvements in ultra-low wear over an extended service life, with dramatically reduced risk of brittle fracture when articulated or moved against articulation surfaces such as the acetabular cup in the case of a hip prosthesis.

In accordance with one preferred formation process, the ceramic or ceramic-based coating is applied to the metal substrate or base material by vapor deposition to mirror the surface finish or smoothness of the base material. In a preferred process, the ceramic or ceramic-based coating is initially applied to the base material by vapor deposition or the like, with a relative thin structure on the order of about 5 microns. The coating is then polished by known techniques to a smoother surface finish and a thinner structure on the order of about 3-4 microns.

Persons skilled in the art will understand and appreciate that the invention can be used in virtually any joint prosthesis, including but not limited to hip, knee, and shoulder prostheses.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 3 is a further enlarged and fragmented sectional view depicting coating details of the metal femoral ball;

FIG. 4 is an enlarged perspective view showing engagement between the femoral ball and an acetabular cup;

DETAILED DESCRIPTION OF THE PREFERRED EMBODIMENTS

Figure 1:
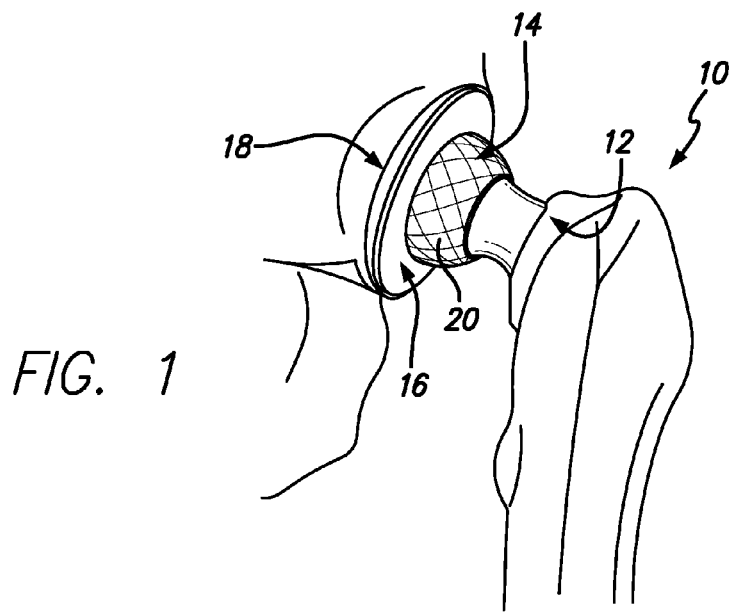
FIG. 1 is a fragmented perspective view illustrating an exemplary joint prosthesis in the form of a hip prosthesis in an installed position affixed to a patient's femur and acetabulum.
Figure 2:
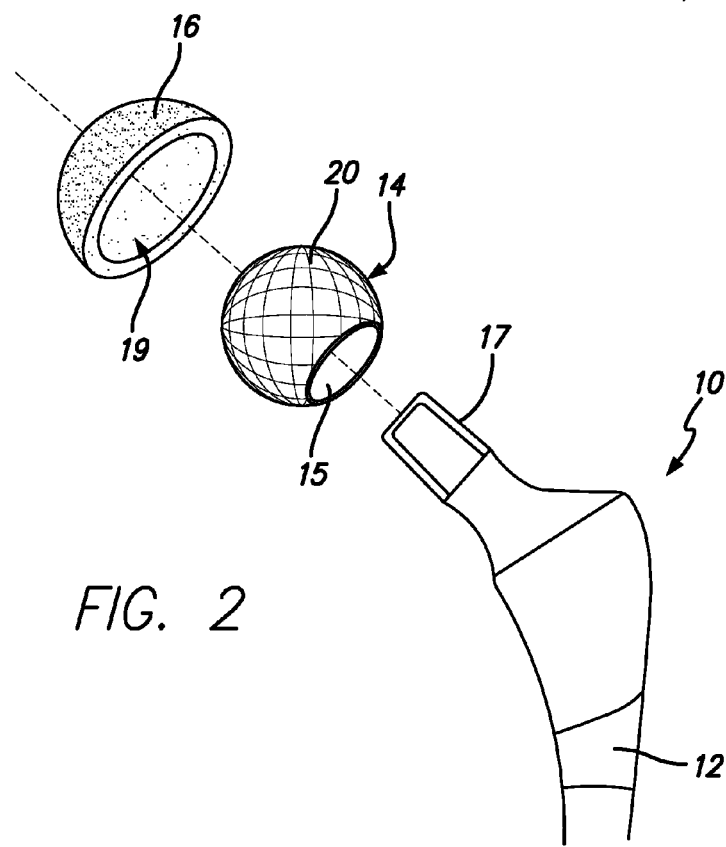
FIG. 2 is an exploded perspective view of a ceramic or ceramic-based coating formed on a metal femoral ball of the femoral component of FIG. 1.

As shown in the exemplary drawings, an improved joint prosthesis in the form of the illustrative hip prosthesis referred to generally by the reference numeral 10 in FIG. 1 includes a femoral component 12 constructed primarily from a biocompatible metal material (such as a cobalt chrome alloy or the like). The metal-based femoral component 12 includes a generally ball-shaped femoral head 14 having a size and shape designed for articulation within an acetabular cup 16 seated and/or affixed within the patient's natural acetabulum or socket 18. The metal-based femoral component 12 comprises the articulatory component of the joint prosthesis, and an outer articulatory surface thereof is surface-coated with a relatively thin film ceramic coating 20 (FIGS. 2-4).

FIG. 1 illustrates a traditional hip prosthesis 10 for use in repairing or replacing the natural anatomical ball-and-socket human hip joint. The ceramic coating 20 on the articulatory surface of the femoral ball-shaped head 14 engages with a generally matingly shaped concave surface 19 of the acetabular cup 16. The head 14 can be formed as a separate component, e.g., as shown, with an open-sided cavity 15 to press-fit receive a neck 17 of the femoral component 12. Alternately, if desired, the head 14 can be formed integrally with the femoral component 12.

In the preferred form, the ceramic coating comprises a relatively thin film coating of a doped silicon nitride ($Si_3N_4$) as disclosed in U.S. Pat. No. 6,881,229, which is incorporated by reference herein. This high strength and high toughness doped silicon nitride ceramic coating provides improvements in ultra-low wear over an extended service life, with dramatically reduced risk of brittle fracture when articulated or moved against articulation surfaces such as the acetabular cup 16 in the case of the illustrative hip prosthesis 10.

The ceramic coating 20 is applied to the articulatory or convex surface of the head 14 preferably by vapor deposition using known techniques to achieve a thin film or layer on the order of about 5 microns. The vapor deposition process beneficially deposits the ceramic film with a surface finish that essentially mirrors the surface finish of the articulatory component to which it is applied, such as the head 14 of the femoral prosthesis 12. After thin film deposition, the ceramic coating 20 can be polished using any suitable known technique to a smoother surface finish, if desired, and a thinner film layer on the order of about 3-4 microns (FIGS. 3-4).

Persons skilled in the art will understand and appreciate that the invention can be employed in virtually any implanted joint prosthesis, such as a hip, knee, or shoulder prosthesis, with the articulatory component being surface-coated with the thin film ceramic or ceramic-based coating to provide improvement in ultra-low wear over an extended service life. The ceramic or ceramic-based coating on the articulatory surface of the joint prosthesis can engage natural patient bone/cartilage, or alternatively engage a matingly shaped prosthesis component formed from a polymer-based bearing component, a biocompatible metal-based material, or a similar ceramic or ceramic-based material.

Figure 5:
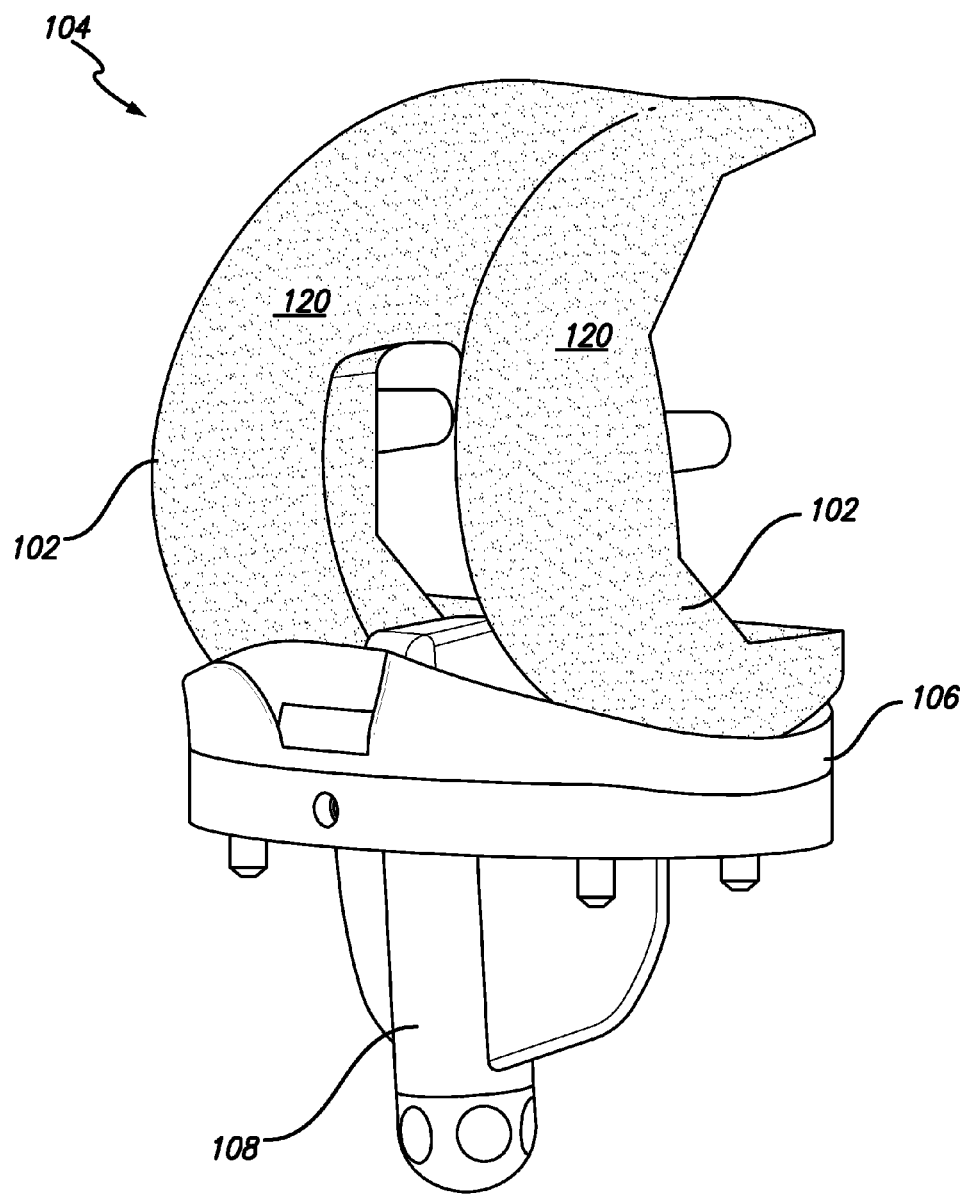
FIG. 5 is a perspective view of a knee implant prosthesis having the ceramic or ceramic-based coating formed on an articulatory surface thereof.

FIG. 5 shows an exemplary knee implant referred to by reference numerals increased by 100. As shown, the laterally spaced condyles 102 on a femoral component 104 include the surface coating 120 formed as by vapor deposition onto the underside surfaces of the metal-based condyles 102 and suitably polished to a surface finish mirroring the initial surface finish of the metal condyles 102. The surface coating 120 is shown to engage a bearing component 106 such as high density polyethylene or the like supported on a tibial component 108.

Figure 6:
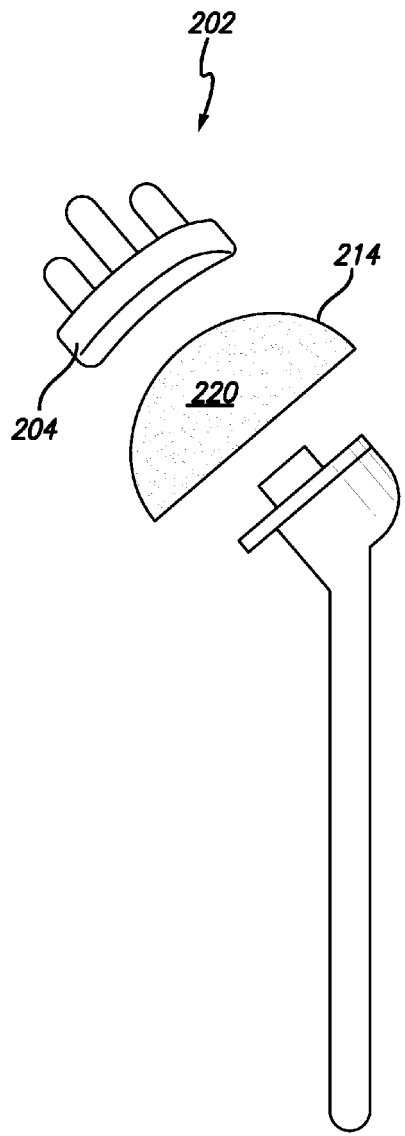
FIG. 6 is an exploded side view of a shoulder implant prosthesis having the ceramic or ceramic-based coating formed on an articulatory surface of a metal-based head.
Figure 7:
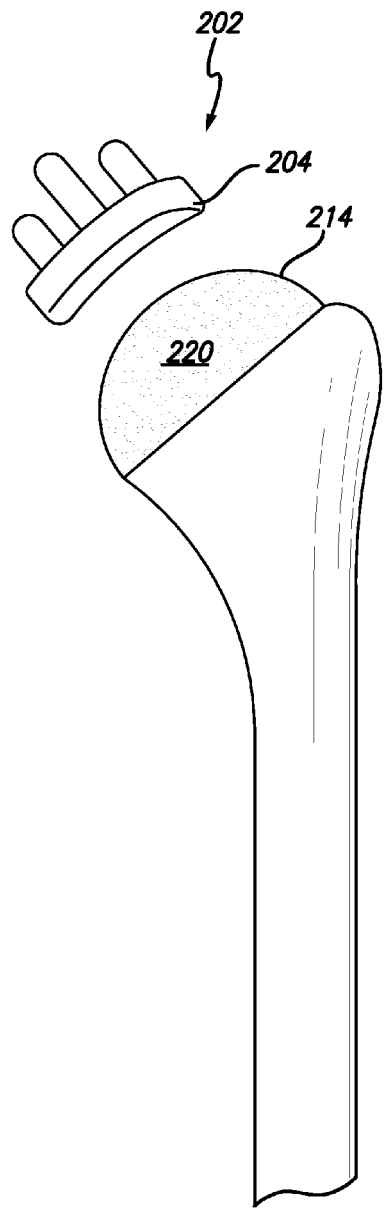
FIG. 7 is a partially exploded side view similar to FIG. 6, wherein a ball-shaped head is mounted for articulatory engagement with a socket cup.

FIGS. 6 and 7 show an exemplary shoulder implant referred to by reference numerals increased by 200. As shown, a ball-shaped head 214 of a shoulder component 202 includes the surface coating 220 formed as by vapor deposition onto the articulatory surface on the metal-based head 214 and suitably polished to a surface finish mirroring the initial surface finish of the head 214. The surface coating 220 is shown to engage a socket cup 204 or the like suitably implanted into the user's shoulder.

A variety of further modifications and improvements in and to the joint prosthesis of the present invention will be apparent to persons skilled in the art. Accordingly, no limitation on the invention is intended by way of the foregoing description and accompanying drawings, except as set forth in the appended claims.

What is claimed is:

1. A joint prosthesis, comprising:
    an articulatory component defining an articulatory surface for moving, when implanted into the human body, against a non-articulating surface;
    said articulatory surface comprising a thin film surface ceramic coating of doped silicon nitride ($Si_3N_4$) polished to a relatively smooth surface finish and applied to a base material,
    wherein said doped silicon nitride ($Si_3N_4$) has a flexural strength greater than about 700 Mega-Pascal (MPa) and a toughness greater than about 7 Mega-Pascal root meter ($MPam^{0.5}$),
    wherein said base material comprises a base metal material surface-coated with said doped silicon nitride coating ($Si_3N_4$) and polished to a surface finish substantially mirroring the surface finish of said base metal material, and
    wherein said thin film ceramic coating of doped silicon nitride ($Si_3N_4$) is vapor deposited onto said base metal material at a thickness on the order of about 5 microns and is polished to a thickness on the order of about 3-4 microns.

2. The joint prosthesis of claim 1 wherein said articulatory surface comprises an articulatory surface of a hip implant.

3. The joint prosthesis of claim 1 wherein said articulatory surface comprises an articulatory surface of a knee implant.

4. The joint prosthesis of claim 1 wherein said articulatory surface comprises an articulatory surface of a shoulder implant.

5. A process of making a joint prosthesis, comprising the steps of:
    forming an articulatory surface on a joint prosthesis, for moving, when implanted into the human body, against a non-articulating surface;
    said articulatory surface comprising a thin film surface ceramic coating of doped silicon nitride ($Si_3N_4$) polished to a relatively smooth surface finish and applied to a base material,
    wherein said doped silicon nitride ($Si_3N_4$) has a flexural strength greater than about 700 Mega-Pascal (MPa) and a toughness greater than about 7 Mega-Pascal root meter ($MPam^{0.5}$),
    wherein said base material comprises a base metal material surface-coated with said doped silicon nitride coating ($Si_3N_4$) and polished to a surface finish substantially mirroring the surface finish of said base metal material, and wherein said thin film ceramic coating of doped silicon nitride (Si$_3$N$_4$) is vapor deposited onto said base metal material at a thickness on the order of about 5 microns and is polished to a thickness on the order of about 3-4 microns.

6. The process of claim 5 wherein said articulatory surface comprises an articulatory surface of a hip implant.

7. The process of claim 5 wherein said articulatory surface comprises an articulatory surface of a knee implant.

8. The process of claim 5 wherein said articulatory surface comprises an articulatory surface of a shoulder implant.

9. A knee prosthesis, comprising:
   an articulatory component defining an articulatory surface for moving, when implanted into the human body, against a non-articulating surface;
   said articulatory surface comprising a thin film surface ceramic coating of doped silicon nitride (Si$_3$N$_4$) polished to a relatively smooth surface finish and applied to a base metal material, wherein said doped silicon nitride (Si$_3$N$_4$) has a flexural strength greater than about 700 Mega-Pascal (MPa) and a toughness greater than about 7 Mega-Pascal root meter (MPam$^{0.5}$), wherein said base material comprises a base metal material surface-coated with said doped silicon nitride coating (Si$_3$N$_4$) and polished to a surface finish substantially mirroring the surface finish of said base metal material, and wherein said thin film ceramic coating of doped silicon nitride (Si$_3$N$_4$) is vapor deposited onto said base metal material at a thickness on the order of about 5 microns and is polished to a thickness on the order of about 3-4 microns.

\* \* \* \* \*